United States Patent
Bodas et al.

(10) Patent No.: US 11,358,916 B2
(45) Date of Patent: Jun. 14, 2022

(54) PROCESS FOR N-BUTANIZING FIELD BUTANE FEEDSTOCK TO THERMAL CRACKERS

(71) Applicant: SABIC Global Technologies B.V., Bergen op Zoom (NL)

(72) Inventors: Vijay Dinkar Bodas, Riyadh (SA); Sultan Al-Otaibe, Riyadh (SA); Guillermo Leal, Riyadh (SA); Mohammed Bismillah Ansari, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/047,001

(22) PCT Filed: Apr. 23, 2019

(86) PCT No.: PCT/IB2019/053336
§ 371 (c)(1),
(2) Date: Oct. 12, 2020

(87) PCT Pub. No.: WO2019/207477
PCT Pub. Date: Oct. 31, 2019

(65) Prior Publication Data
US 2021/0147317 A1    May 20, 2021

Related U.S. Application Data (60) Provisional application No. 62/663,845, filed on Apr. 27, 2018.

(51) Int. Cl.
*C07C 4/04*    (2006.01)
*B01D 3/14*    (2006.01)
(Continued)

(52) U.S. Cl.
CPC .............. *C07C 4/04* (2013.01); *B01D 3/146* (2013.01); *C07C 5/2702* (2013.01); *C07C 7/005* (2013.01); *C07C 7/04* (2013.01)

(58) Field of Classification Search
CPC .. C07C 9/10; C07C 4/04; C07C 7/005; C07C 7/04; C07C 5/2713; C07C 5/2724;
(Continued)

(56) References Cited

U.S. PATENT DOCUMENTS 3,238,735 A * 3/1966 Siewert .................. C07C 7/04
                                                              62/623
4,191,845 A * 3/1980 Rubin ...................... C07C 5/03
                                                             585/251
(Continued)

FOREIGN PATENT DOCUMENTS

EP          2062865 A1    5/2009
WO    WO2016038213 A1    3/2016

OTHER PUBLICATIONS

International Search Report and Written Opinion from PCT/IB2019/053336 dated Aug. 7, 2019, 9 pages.

*Primary Examiner* — Sharon Pregler
(74) *Attorney, Agent, or Firm* — Norton Rose Fulbright US LLP (57) ABSTRACT

Described is a process for producing field butane. The process includes increasing the n-butane concentration in field butane. The process may include a concentration process that includes distillation and a thermal cracking process.

19 Claims, 4 Drawing Sheets

(51) Int. Cl.
*C07C 5/27* (2006.01)
*C07C 7/00* (2006.01)
*C07C 7/04* (2006.01)

(58) Field of Classification Search
CPC ... C07C 5/2727; C07C 11/04; C07C 2523/42; C07C 2527/053; C07C 2531/02; C07C 5/2702; B01D 3/146
See application file for complete search history.

(56) References Cited

U.S. PATENT DOCUMENTS

| | | |
|---|---|---|
| 4,336,046 A | 6/1982 | Schorre et al. |
| 4,773,968 A | 9/1988 | O'Connell et al. |
| 2011/0040133 A1* | 2/2011 | Vermeiren ............ C07C 11/04 585/304 |

* cited by examiner

PROCESS FOR N-BUTANIZING FIELD BUTANE FEEDSTOCK TO THERMAL CRACKERS

CROSS REFERENCE TO RELATED APPLICATIONS

This application is a national phase application under 35 U.S.C. § 371 of International Application No. PCT/IB2019/053336 filed Apr. 23, 2019, which claims priority to U.S. Provisional Patent Application No. 62/663,845 filed Apr. 27, 2018. The entire contents of each of the above-referenced disclosures is specifically incorporated by reference herein without disclaimer.

FIELD OF INVENTION

The present invention generally relates to producing field grade butane (field butane). More specifically, the present invention relates to increasing the concentration of n-butane in field butane.

BACKGROUND OF THE INVENTION

Field butane is a product that primarily includes n-butane or a mixture of n-butane and isobutane. Typically, field butane is obtained from gas oil separation plants. Gas oil separation plants typically include a sulfur removal system and a depropanizer unit. The field butane is supplied from the gas oil separation plants as piped liquid at room temperature and at a pressure above that required to maintain the butane in liquid phase.

Field butane is usually delivered from the gas oil separation plant's depropanizer bottom to market. Typically, the ratio of linear hydrocarbon/branched hydrocarbon in this field butane supplied to the market is about 2.34. Field butane may be used as a blending component in gasoline; but it has low octane value. The field butane blending limit in gasoline is about 4%. Surplus field butane may be sold in the LPG market, used for methyl tertiary butyl ether (MTBE) manufacture or re-injected in the oil field. Field butane may also be used as a thermal cracking feedstock. It is well known that branched hydrocarbon feedstock does not crack as well as linear hydrocarbon feedstock.

BRIEF SUMMARY OF THE INVENTION

A method has been discovered that increases the ratio of linear butane/branched butane in field butane. By increasing this ratio, the utilization efficiency of field butane as feedstock to thermal cracking units can be improved.

Embodiments of the invention include a method of increasing n-butane concentration in field butane. The method may comprise subjecting a feed stream, comprising primarily n-butane and isobutane collectively, to a concentrating process, the concentrating process comprises distilling, in one or more distillation columns, and produces a first product stream comprising primarily n-butane and a second product stream that may comprise methane, ethane, and propane. The method may further include cracking, in a thermal cracker, the first product stream to produce a third product stream comprising primarily ethylene and a fourth product stream comprising primarily n-butane. The method may further include recycling, from the thermal cracker, at least some of the fourth product stream to the first distillation column.

Embodiments of the invention include a method of increasing n-butane concentration in field butane. The method may comprise subjecting a feed stream, comprising primarily n-butane and isobutane collectively, to a concentrating process, the concentrating process comprises distilling, in one or more distillation columns, and produces a first product stream comprising primarily n-butane and a second product stream that may comprise methane, ethane, and propane. The distilling may include distilling, in a first distillation column, a combined stream that comprises a mixture of the first feed stream and a recycle stream having primarily isobutane to produce a bottoms stream comprising primarily n-pentane, an intermediate stream comprising primarily n-butane, and an overhead stream comprising primarily isobutane. The concentrating may further include combining the intermediate stream and the bottoms stream to produce the first product stream, isomerizing the overhead stream in a reactor to convert at least some of the overhead stream's isobutane to n-butane, and distilling, in a second distillation column, effluent from the reactor to form the recycle stream and the second product stream. The method may further include cracking, in a thermal cracker, the first product stream to produce a third product stream comprising primarily ethylene and a fourth product stream comprising primarily n-butane. The method may further include recycling, from the thermal cracker, at least some of the fourth product stream to the first distillation column.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1:
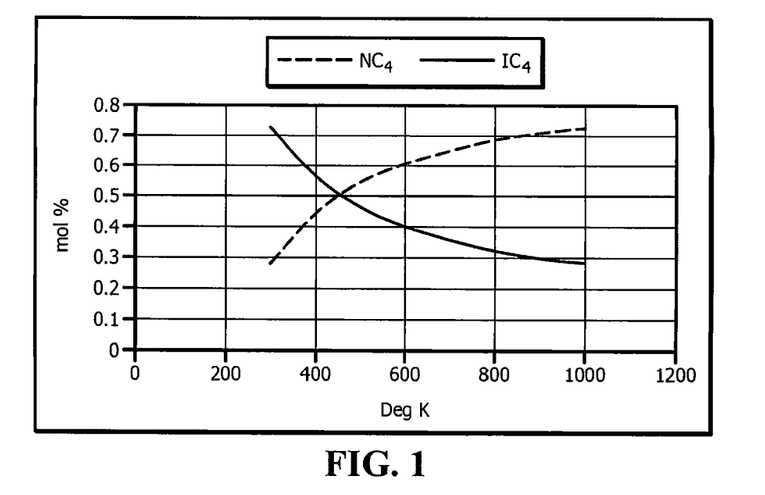
FIG. 1 shows equilibrium data for butane isomers.

FIG. 1 shows equilibrium data for butane isomers. As can be seen from FIG. 1, higher temperature favors n-butane formation over isobutane formation. Thus, for an isomer separation column used to purify a particular throughput of a mixture of n-butane/butane isomers, as temperature increases, the size of the isomer separation column required decreases. However, as temperature increases, hydrocracking and formation of light ends increases. Thus, arriving at the ideal operating temperature involves counter balancing these two effects. Some research suggests that the ideal temperature to separate n-buttane and isobutane is less than 300° C.

Some commercially available processes utilize shape selectivity of zeolites to increase branched hydrocarbon content as opposed to linear hydrocarbon content. However, for processes in which hydrocarbons are to be cracked, a high linear hydrocarbon/branched hydrocarbon ratio is preferred. Thus, the use of zeolite as a catalyst is undesirable for producing feedstock for these cracking processes.

A method has been discovered that increases the ratio of linear butane/branched butane in field butane. By increasing this ratio, the utilization efficiency of field butane as feedstock to thermal cracking units can be improved.

Figure 2:
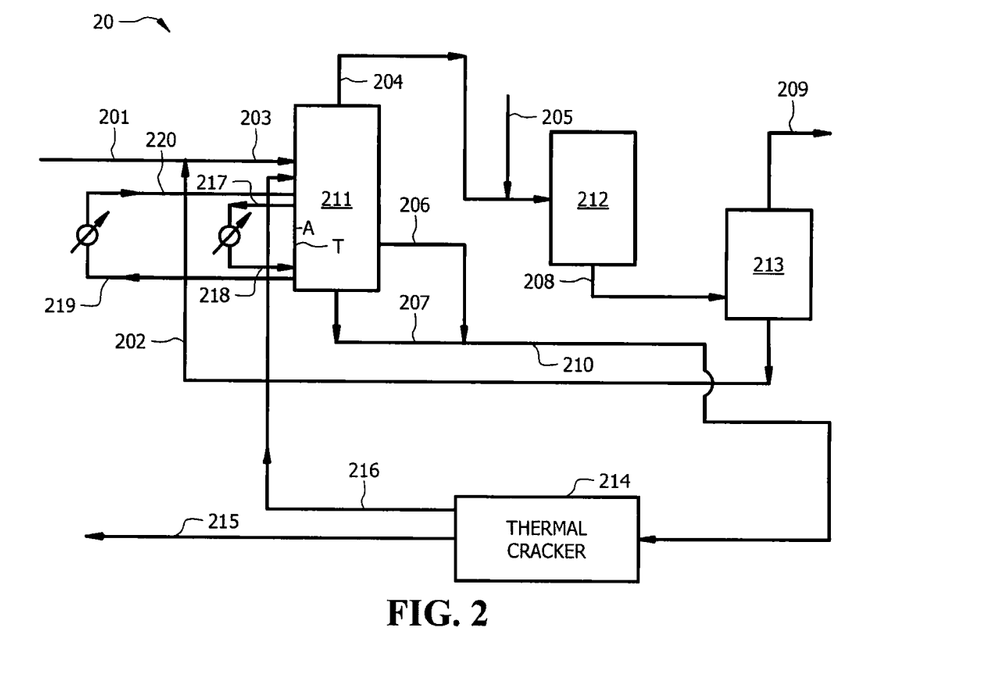
FIG. 2 shows a system for increasing n-butane concentration in field butane, according to embodiments of the invention.
Figure 3:
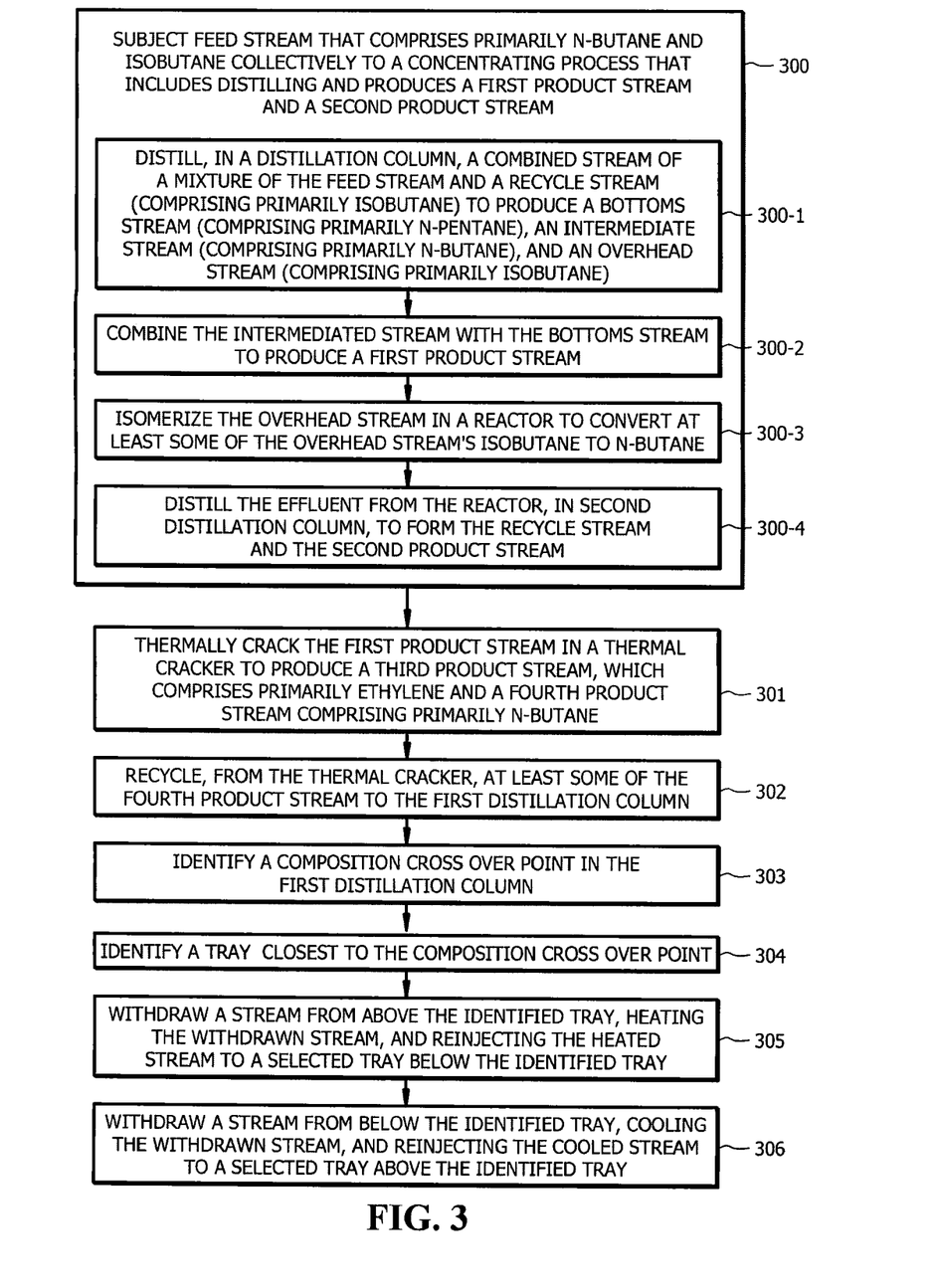
FIG. 3 shows a method for increasing n-butane concentration in field butane, according to embodiments of the invention.

FIG. 2 shows system 20 for increasing n-butane concentration in field butane, according to embodiments of the invention. FIG. 3 shows method 30 for increasing n-butane concentration in field butane, according to embodiments of the invention. Method 30 may be implemented using system 20.

Method 30, as implemented by system 20, may begin at block 300, which involves subjecting feed stream 201, comprising primarily n-butane and isobutane collectively, to a concentrating process, the concentrating process includes distilling, in one or more distillation columns, and produces first product stream 210, which comprises primarily n-butane, and second product stream 209, which may comprise methane, ethane, and propane. In embodiments of the invention, feed stream 201 may further include propane and n-pentane. In embodiments of the invention, feed stream 201 may include 62 mol. % to 72 mol. % n-butane and 24 mol. % to 34 mol. % isobutane. In embodiments of the invention, the n-butane/isobutane mol. ratio of feed stream 201 is in a range a range 1.8 to 2.8. In embodiments of the invention, feed stream 201 comprises 94 mol. % to 98 mol. % n-butane and isobutane collectively. In embodiments of the invention, feed stream 201 further comprises n-pentane and/or propane.

According to embodiments of the invention, at block 301, first product stream 210 is thermally cracked in thermal cracker 214 to produce third product stream 215, which comprises primarily ethylene and fourth product stream 216, which comprises primarily n-butane. Method 30 may further include, at block 302, recycling, from thermal cracker 214, at least some of fourth product stream 216 to distillation column 211.

Block 300 may include blocks 300-1 to 300-4. In embodiments of the invention, the concentrating process of block 300 includes, at block 300-1, distilling, in distillation column 211, combined stream 203, which comprises a mixture of feed stream 201 and recycle stream 202 (comprising primarily isobutane) to produce bottoms stream 207 (comprising primarily n-pentane), intermediate stream 206 (comprising primarily n-butane), and overhead stream 204 (comprising primarily isobutane). In embodiments of the invention, overhead stream 204 comprises 94 mol. % to 98 mol. % isobutane and 2 mol. % to 6 mol. % propane; the intermediate stream comprises 96 mol. % to 100 mol. % n-butane; and the bottoms stream comprises 96 mol. % to 100 mol. % n-pentane.

In embodiments of the invention, at block 300-2, intermediate stream 206 is combined with bottoms stream 207 to produce first product stream 210. In embodiments of the invention, first product stream 210 comprises 85 mol. % to 95 mol. % n-butane. First product stream 210 may also include n-pentane, methane, ethane, and propane.

Method 30 may further include, at block 300-3, isomerizing overhead stream 204 in reactor 212 to convert at least some of overhead stream 204's isobutane to n-butane. In embodiments of the invention, the isomerizing includes mixing overhead stream 204 with hydrogen 205 and contacting this mixture with a catalyst under reaction conditions sufficient to isomerize at least some of the isobutane to n-butane. According to embodiments of the invention, the catalyst used in isomerizing the isobutane may include a selection from the list consisting of: sulfated zirconia, platinum on alumina, platinum on alumina dosed with perchloroethylene or other chlorinating agent, flouridized catalyst, and combinations thereof. However, in embodiments of the invention the catalyst used does not contain zeolite because zeolite favors formation of branched hydrocarbons. The reaction conditions for the isomerization process in reactor 212 may include a reaction temperature of 130 to 300° C., a pressure of 10 to 30 bar and GHSV of 4.0 to 5.5. In embodiments of the invention, effluent 208 from reactor 212 comprises 42 mol. % to 52 mol. % isobutane and 35 mol. % to 45 mol. % n-butane.

Method 30 may also include, at block 300-4, distilling effluent 208 from reactor 212, in distillation column 213, to form recycle stream 202 and second product stream 209. According to embodiments of the invention, recycle stream 202 may comprise 48 mol. % to 58 mol. % isobutane and 42 mol. % to 52 mol. % n-butane. According to embodiments of the invention, second product stream 209 may comprise 5 mol. % to 15 mol. % methane, 15 mol. % to 25 mol. % ethane, and 65 mol. % to 75 mol. % propane.

In embodiments of the invention, first product stream 210 is flowed to thermal cracker 214. As noted above, in thermal cracker 214, block 301 may be implemented, which involves cracking first product stream 210 to produce third product stream 215 and fourth product stream 216. Third product stream 215 may comprise primarily ethylene and fourth product stream 216 may comprise primarily n-butane. In embodiments of the invention, third product stream 215 comprises 52 wt. % to 58 wt. % ethylene. In embodiments of the invention fourth product stream 216 comprises 98 mol. % to 99.8 mol. % n-butane. At block 302, method 30 may involve, recycling, from thermal cracker 214, at least some of fourth product stream 216 to distillation column 211.

Figure 4:
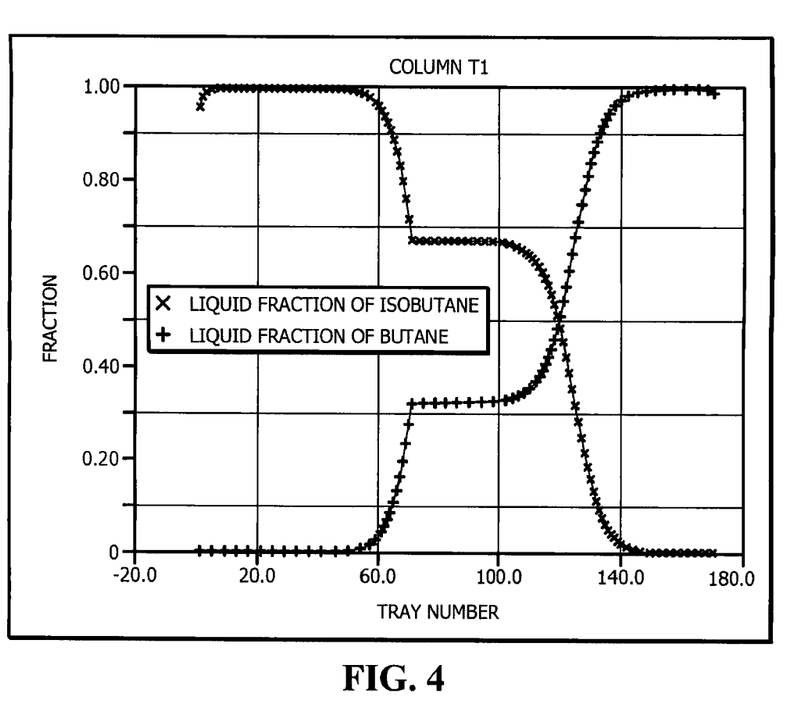
FIG. 4 shows a graph related to a simulation of distilling a n-butane/isobutane mixture, according to embodiments of the invention.

According to embodiments of the invention, method 30 may involve, at block 303, identifying a composition cross over point in the first distillation column. Block 304 may then involve identifying a tray closest to the composition crossover point in distillation column 211. FIG. 4 shows a graph related to a simulation of distilling a n-butane/isobutane mixture, according to embodiments of the invention. The graph shows a cross over point in the distillation column of the simulation.

Embodiments of the invention may include, as shown at block 305, withdrawing stream 217 from above identified tray T, heating withdrawn stream 217, and reinjecting heated stream 218 to a selected tray below identified tray T. Alternatively or additionally, method 30 may include, at block 306, withdrawing stream 219 from below the identified tray, cooling withdrawn stream 219, and reinjecting the cooled stream 220 to a selected tray above the identified tray T.

If reboil or reflux control starts overfeeding in distillation column 211, because such a column is typically large, the reboil or reflux may not be discovered before distillation column 211 gets filled up with a large liquid inventory such as LPG. This large LPG accumulation increases risk of a safety incident as compared to the risk associated with the original design of distillation column 211. Thus, it is desirable to provide mitigating steps that avoid such accumulation of LPG.

The mitigation steps may include, before deploying a control scheme, running a final simulation that incorporates all changes brought in by methods described herein and re-estimate the composition crossover temperature. The composition crossover temperature can be used as a reference temperature to find the difference between operating value and a simulated design value. If this difference starts to show a cooling off, the reflux is too much and if it starts to show overheating, the reboil is too much.

To control reflux, add a signal via small feedforward summer block, the cooling off temperature difference value at the composition crossover point, to the output of the conventional reflux controller.

To control reboil, add a signal via small feedforward summer block, the overheated temperature difference value at the composition crossover point, to the output of the conventional reboiler heat input controller.

The vessel design pressure is usually a safety factor above operating. The butane vapor pressures are such that the distillation column can be designed for conventional air/water cooling and steam heating. However, seasonal and daily variations in ambient conditions mean that the column will usually have the need for internal reflux control. This will match the vapor leaving thermal conditions from column top with reflux return thermal conditions. The practical impact of this scheme is either increased throughput or reduced column condenser and reboiler duty, depending on what is desired. At the design stage, this scheme clearly opts for reduced reflux and reboiler duty.

The estimated impact of the methods described herein is to reduce the cost of separation by about 40%+, thereby capital efficiency of this process improves.

Although embodiments of the present invention have been described with reference to blocks of FIG. 3, it should be appreciated that operation of the present invention is not limited to the particular blocks and/or the particular order of the blocks illustrated in FIG. 3. Accordingly, embodiments of the invention may provide functionality as described herein using various blocks in a sequence different than that of FIG. 3.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Material Balance of the Concentration Process

Table 1 below shows a simulated material balance for the concentration process as described with respect to block 300 above.

TABLE 1

| | | | | | DIB Column | | | | | |
|---|---|---|---|---|---|---|---|---|---|---|
| | H2 | Field Butanes | Feed + Rec | Ovhd | Side draw | Bottom | Rx exit | Scrub ovhd | Recycle | nButane |
| Stream # | 5 mol % | 1 mol % | 3 mol | 4 mol | 6 mol | 7 mol | 8 mol | 9 mol | 2 mol | 9 + 10 mol | nButane |
| H2 | 100.00% | | | | | | | | | | |
| CH4 | | | | | | | 1.12% | 10.05% | 0.00% | 0.70% | 0.20% |
| C2H6 | | | | | | | 2.23% | 20.10% | 0.00% | 1.39% | 0.74% |
| C3H8 | | 2.62% | 1.68% | 4.25% | | | 7.75% | 69.85% | 0.00% | 4.84% | 3.75% |
| isobutane | | 28.87% | 37.76% | 95.75% | | | 47.54% | | 53.47% | | |
| nButane | | 67.70% | 60.05% | | 100.00% | | 41.36% | | 46.53% | 92.28% | 94.32% |
| Isopentane | | | | | | | | | | | |
| nPentane | | 0.30% | 0.51% | | | 100.00% | | | | 0.79% | 1.00% |
| neopentane | | | | | | | | | | | |
| CyPentane | | | | | | | | | | | |
| Cis2Pentene | | | | | | | | | | | |
| nHexane | | | | | | | | | | | |
| Total | 100.00% | 100.00% | 100.00% | 100.00% | 100.00% | 100.00% | 100.00% | 100.00% | 100.00% | 100.00% | 100.00% |
| MW Kg/Kgmol | 2.02 | 57.87 | 57.96 | 57.53 | 58.12 | 72.15 | 55.94 | 38.46 | 58.12 | 56.87 | |
| t/h @ 286 t/h feed | 0.34 | 305.00 | 478.20 | 187.16 | 287.98 | 3.05 | 187.50 | 14.31 | 173.20 | 305.34 | 305.34 |

Example 2

Distillation Column

Figure 5:
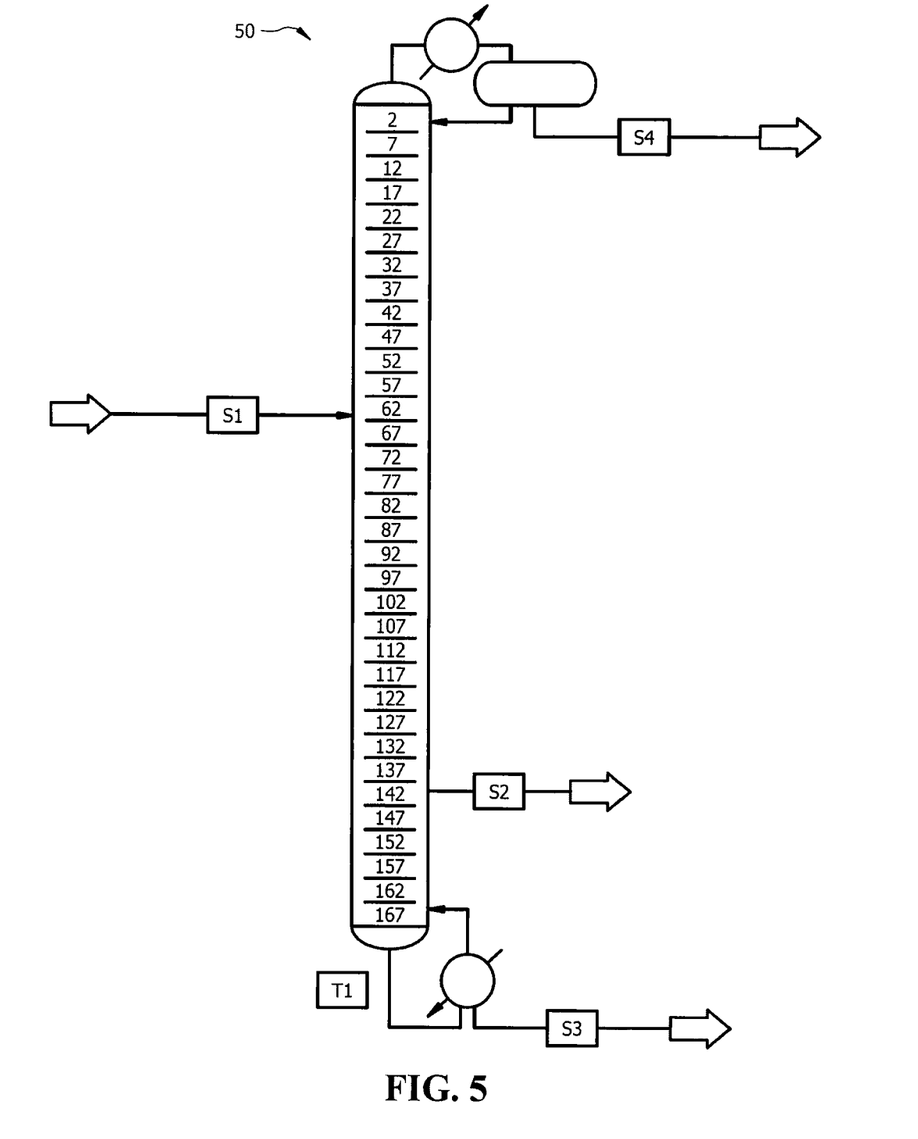
FIG. 5 shows a distillation column for performing the separation of n-butane and isobutane, according to embodiments of the invention.

FIG. 5 shows distillation column 50 for performing the separation of n-butane and isobutane, according to embodiments of the invention. Distillation column 40 may be used to function as distillation column 211 in system 20 to carry out the distillation described in block 300-1 of method 30. Table 2 below shows a simulation of the separation duty for distillation column 50 in implementing the distillation described in block 300-1 of method 30.

TABLE 2

| Stream ID | | S1 | S2 | S3 | S4 |
|---|---|---|---|---|---|
| Phase | | Liquid | Liquid | Liquid | Liquid |
| TEMPERATURE, | C. | 45.0 | 62.7 | 62.9 | 47.7 |
| PRESSURE, | KG/CM2 | 7.1 | 7.0 | 7.0 | 7.0 |
| RATE, | KG-MOL/HR | 7757.69 | 176.53 | 4521.51 | 3059.65 |
| COMP. MOLE FRACTIONS | | | | | |
| 1 | H2 | 0 | 0 | 0 | 0 |
| 2 | METHANE | 0 | 0 | 0 | 0 |
| 3 | ETHANE | 0 | 0 | 0 | 0 |
| 4 | PROPANE | 0.0168 | 0 | 0 | 0.0426 |
| 5 | ISOBUTAN | 0.3776 | 1.86E−07 | 1.11E−08 | 0.9574 |
| 6 | BUTANE | 0.6005 | 0.9987 | 0.9913 | 4.59E−06 |
| 7 | NEOPENTA | 0 | 0 | 0 | 0 |
| 8 | IPENTANE | 0 | 0 | 0 | 0 |
| 9 | PENTANE | 5.10E−03 | 1.29E−03 | 8.70E−03 | 0 |
| 10 | CP | 0 | 0 | 0 | 0 |
| 11 | HEXANE | 0 | 0 | 0 | 0 |
| | Total | 1 | 1 | 1 | 1 |

Table 3 shows results of a simulation to implement method 30. The results show 8.5% increased ethylene production in a mixed feed cracker from the same quantity of feedstock. This demonstrates an improved feedstock utilization efficiency when method 30 is used.

TABLE 3

| | Product Slate: | | | |
|---|---|---|---|---|
| | As supplied KTA | n-Butanized KTA | Delta KTA | $/MT |
| Ethylene | 1527.85 | 1656.95 | 129.10 | 800 |
| Propylene | 663.37 | 652.62 | −10.75 | 540 |

TABLE 3-continued

| | | | | |
|---|---|---|---|---|
| 13BD | 0.00 | 0.00 | 0.00 | |
| Benzene | 118.45 | 102.33 | −16.11 | 590 |
| Million US$ Incremental income | | | | 87.97 |
| Feed | | | | |
| Ethane t/h | 75.598 | 75.598 | | |
| Butane t/h | 305.188 | 305.188 | | |

| | Field Butane feed composition basis | |
|---|---|---|
| | As supplied wt % | n-Butanized wt % |
| CH4 | | 0.20% |
| C2H6 | | 0.74% |
| C3H8 | 2.62% | 3.75% |
| isobutane | 28.87% | |
| nButene | 67.70% | 94.32% |
| Isopentane | 0.00% | |
| nPentane | 0.80% | 1.00% |
| | 100.00% | 100.00% |

In the context of the present invention, embodiments 1-19 are described. Embodiment 1 is a method of increasing n-butane concentration in field butane. The method includes subjecting a feed stream, comprising primarily n-butane and isobutane collectively, to a concentrating process, the concentrating process including distilling, in one or more distillation columns, and producing a first product stream containing primarily n-butane and a second product stream comprising methane, ethane, and propane. The process also includes cracking, in a thermal cracker, the first product stream to produce a third product stream comprising primarily ethylene and a fourth product stream comprising primarily n-butane. The process further includes recycling, from the thermal cracker, at least some of the fourth product stream to the one or more distillation columns. Embodiment 2 is the method of embodiment 1, wherein the concentrating process includes distilling, in a first distillation column, a combined stream that includes a mixture of the feed stream and a recycle stream having primarily isobutane to produce a bottoms stream comprising primarily n-pentane, an intermediate stream comprising primarily n-butane, and an overhead stream comprising primarily isobutene. The method further includes combining the intermediate stream and the bottoms stream to produce the first product stream, isomerizing the overhead stream in a reactor to convert at least some of the overhead stream's isobutane to n-butane, and distilling effluent from the reactor, in a second distillation column, to form the recycle stream and the second product stream. Embodiment 3 is the method of embodiment 2, wherein the isomerizing includes mixing the overhead stream with hydrogen to form a combination and contacting the combination with a catalyst under reaction conditions to isomerize at least some of the isobutane to n-butane. Embodiment 4 is the method of embodiment 3, wherein the catalyst does not include zeolite and is a selection from the list consisting of: sulfated zirconia, platinum on alumina, platinum on alumina dosed with perchloroethylene or other chlorinating agent, flouridized catalyst, and combinations thereof. Embodiment 5 is the method of either of embodiments 3 or 4, wherein the reaction conditions include a reaction temperature of 130 to 300° C., a pressure of 10 to 30 bar and GHSV of 4 to 5.5. Embodiment 6 is the method of any of embodiments 2 to 5, wherein effluent from the reactor contains 42 mol. % to 52 mol. % isobutane and 35 mol. % to 45 mol. % n-butane. Embodiment 7 is the method of any of embodiments 2 to 6, wherein the recycle stream includes 48 mol. % to 58 mol. % isobutane and 42 mol. % to 52 mol. % n-butane. Embodiment 8 is the method of any of embodiments 1 to 7, wherein the n-butane/isobutane mol. ratio in field butane is in a range a range 1.8 to 2.8 and wherein the first product stream comprises 85 mol. % to 95 mol. % n-butane. Embodiment 9 is the method of any of embodiments 1 to 8, wherein the feed stream contains 62 mol. % to 72 mol. % n-butane and 24 mol. % to 34 mol. % isobutane and wherein the first product stream contains 85 mol. % to 95 mol. % n-butane. Embodiment 10 is the method of any of embodiments 1 to 9, wherein the feed stream contains 94 mol. % to 98 mol. % n-butane and isobutane collectively. Embodiment 11 is the method of any of embodiments 1 to 10, wherein the feed stream further includes n-pentane. Embodiment 12 is the method of any of embodiments 1 to 11, wherein the second product stream further includes 5 mol. % to 15 mol. % methane, 15 mol. % to 25 mol. % ethane, and 65 mol. % to 75 mol. % propane. Embodiment 13 is the method of any of embodiments 1 to 12, wherein the overhead stream contains 94 mol. % to 98 mol. % isobutane and 2 mol. % to 6 mol. % propane. Embodiment 14 is the method of any of embodiments 1 to 13, wherein the intermediate stream contains 96 mol. % to 100 mol. % n-butane. Embodiment 15 is the method of any of embodiments 1 to 14, wherein the bottoms stream contains 96 mol. % to 100 mol. % n-pentane. Embodiment 16 is the method of any of embodiments 1 to 15, wherein the fourth product stream contains 98 mol. % to 99.8 mol. % n-butane. Embodiment 17 is the method of any of embodiments 2 to 16, wherein the at least some of the fourth product stream is recycled to the first distillation column. Embodiment 18 is the method of any of embodiments 2 to 17, further including identifying a composition crossover point in the first distillation column. The method also includes identifying a tray closest to the composition crossover point in the first distillation column and withdrawing a stream from above the identified tray. The method further includes heating the withdrawn stream and reinjecting the heated stream to a selected tray below the identified tray. Embodiment 19 is the method of any of embodiments 2 to 17, further including identifying a composition crossover point in the first distillation column. The method also includes identifying a tray closest to the composition crossover point in the first distillation column and withdrawing a stream from below the identified tray. The method further includes cooling the withdrawn stream and reinjecting the cooled stream to a selected tray above the identified tray.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of increasing n-butane concentration in field butane, the method comprising:
   subjecting a feed stream, comprising primarily n-butane and isobutane collectively, to a concentrating process, the concentrating process comprising distilling the feed stream in one or more distillation columns to produce a first product stream comprising primarily n-butane and a second product stream comprising methane, ethane, and propane; and
   cracking, in a thermal cracker, the first product stream to produce a third product stream comprising primarily ethylene and a fourth product stream comprising primarily n-butane; and
   recycling, from the thermal cracker, at least some of the fourth product stream to the one or more distillation columns;
   wherein the concentrating process comprises:
   distilling, in a first distillation column, a combined stream that comprises a mixture of the feed stream and a recycle stream comprising primarily isobutane to produce a bottoms stream comprising primarily n-pentane, an intermediate stream comprising primarily n-butane, and an overhead stream comprising primarily isobutane;
   combining the intermediate stream and the bottoms stream to produce the first product stream;
   isomerizing the overhead stream in a reactor to convert at least some of the isobutane in the overhead stream to n-butane; and
   distilling effluent from the reactor, in a second distillation column, to form the recycle stream and the second product stream.

2. The method of claim 1, wherein the isomerizing includes mixing the overhead stream with hydrogen to form a combination and contacting the combination with a catalyst under reaction conditions to isomerize at least some of the isobutene to n-butane.

3. The method of claim 2, wherein the catalyst does not include zeolite and is a selection from the list consisting of: sulfated zirconia, platinum on alumina dosed with perchloroethylene or other chlorinating agent, flouridized catalyst, and combinations thereof.

4. The method of claim 2, wherein the reaction conditions include a reaction temperature of 130 to 300° C., a pressure of 10 to 30 bar and GHSV of 4 to 5.5.

5. The method of claim 1, wherein effluent from the reactor comprises 42 mol. % to 52 mol. % isobutane and 35 mol. % to 45 mol. % n-butane.

6. The method of claim 1, wherein the recycle stream comprises 48 mol. % to 58 mol. % isobutane and 42 mol. % to 52 mol. % n-butane.

7. The method of claim 1, wherein the n-butane/isobutene mol. ratio in field butane is in a range a range 1.8 to 2.8 and wherein the first product stream comprises 85 mol. % to 95 mol. % n-butane.

8. The method of 1, wherein the feed stream comprises 62 mol. % to 72 mol. % n-butane and 24 mol. % to 34 mol. % isobutene and wherein the first product stream comprises 85 mol. % to 95 mol. % n-butane.

9. The method of 1, wherein the feed stream comprises 94 mol. % to 98 mol. % n-butane and isobutane collectively.

10. The method of 1, wherein the feed stream further comprises n-pentane.

11. The method of 1, wherein the second product stream further comprises 5 mol. % to 15 mol. % methane, 15 mol. % to 25 mol. % ethane, and 65 mol. % to 75 mol. % propane.

12. The method of claim 1, wherein the overhead stream comprises 94 mol. % to 98 mol. % isobutane and 2 mol. % to 6 mol. % propane.

13. The method of claim 1, wherein the intermediate stream comprises 96 mol. % to 100 mol. % n-butane.

14. The method of claim 1, wherein the bottoms stream comprises 96 mol. % to 100 mol. % n-pentane.

15. The method of claim 1, wherein the fourth product stream comprises 98 mol. % to 99.8 mol. % n-butane.

16. The method of claim 1, wherein the at least some of the fourth product stream is recycled to the first distillation column.

17. The method of claim 1, further comprising
   identifying a composition crossover point in the first distillation column;
   identifying a tray closest to the composition crossover point in the first distillation column;
   withdrawing a stream from above the identified tray;
   heating the withdrawn stream; and
   reinjecting the heated stream to a selected tray below the identified tray.

18. The method of claim 1, further comprising:
   identifying a composition crossover point in the first distillation column;
   identifying a tray closest to the composition crossover point in the first distillation column;
   withdrawing a stream from below the identified tray;
   cooling the withdrawn stream; and
   reinjecting the cooled stream to a selected tray above the identified tray.

19. The method of claim 2, further comprising:
   identifying a composition crossover point in the first distillation column;
   identifying a tray closest to the composition crossover point in the first distillation column;
   withdrawing a stream from below the identified tray;
   cooling the withdrawn stream; and
   reinjecting the cooled stream to a selected tray above the identified tray.

* * * * *